United States Patent [19]

Schonenberger et al.

[11] Patent Number: 4,730,068
[45] Date of Patent: Mar. 8, 1988

[54] TUMOR RETARDING (1,2-DIPHENYL-ETHYLENEDIAMINE)-PLATINUM(II)-COMPLEXES

[75] Inventors: Helmut Schonenberger, Pentling; Erwin von Angerer, Grablfing; Johann Karl, Sunching; Margaretha Jennerwein, Regensburg; Jurgen Engel, Alzenau, all of Fed. Rep. of Germany

[73] Assignee: Asta-Werke Aktiengesellschaft, Bielefeld, Fed. Rep. of Germany

[21] Appl. No.: 831,913

[22] Filed: Feb. 21, 1986

[30] Foreign Application Priority Data

Feb. 23, 1985 [DE] Fed. Rep. of Germany ....... 3506507

[51] Int. Cl.$^4$ ............................................. C07F 15/00
[52] U.S. Cl. .................................................... 556/137
[58] Field of Search ......................................... 556/137

[56] References Cited

U.S. PATENT DOCUMENTS

| 4,234,500 | 11/1980 | Hoeschele et al. | 556/137 X |
| 4,250,189 | 2/1981 | Hydes et al. | 556/137 X |
| 4,594,418 | 6/1986 | Speer et al. | 556/137 X |
| 4,598,091 | 7/1986 | Schonenberger et al. | 556/137 X |

FOREIGN PATENT DOCUMENTS 2916145 10/1979 Fed. Rep. of Germany.
3405611 8/1984 Fed. Rep. of Germany.

OTHER PUBLICATIONS

Chemical Abstracts 96 193435; (1982).
Chemical Abstracts 100 203142d, (1984).
Chemical Abstracts 97 33374f, (1982).
Chemical Abstracts 101 203884t, (1984).
Chemical Abstracts 101 122654r, (1984).

*Primary Examiner*—Helen M. S. Sneed
*Attorney, Agent, or Firm*—Cushman, Darby & Cushman

[57] ABSTRACT

There are disclosed antitumor active 1,2-diphenyl-ethylenediamine)-platinum(II)-complex of the general formula

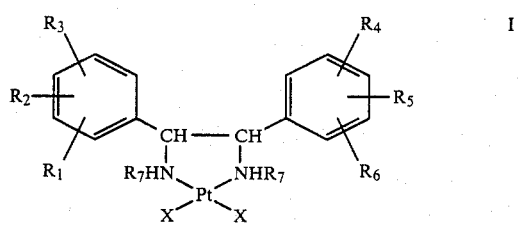

wherein $R_7$ is hydrogen or $C_1$–$C_6$-alkyl and $R_2$ is either (1) a halogen atom and the groups $R_1$, $R_3$, $R_4$, $R_5$, and $R_6$ are the same or different and are hydrogen, halogen, trihalomethyl, $C_1$–$C_6$-alkyl, hydrogen $C_1$–$C_6$-alkoxy, a $C_2$–$C_6$-alkanoyloxy or a halo or $C_1$–$C_4$-alkanesulfonyloxy substituted $C_2$–$C_6$-alkanoyloxy group, or $R_2$ is (2) a hydroxy group, a $C_1$–$C_6$-alkoxy group, a $C_2$–$C_6$-alkanoyloxy group in the 4-position or a halo or $C_1$–$C_4$-alkanesulfonyloxy substituted $C_2$–$C_6$-alkanoyloxy group and if $R_2$ is (2) then the groups $R_1$ and $R_3$ which are the same or differnt are in the 2 and 6 positions of the phenyl group and are halogen, trihalomethyl, $C_1$–$C_6$-alkyl, hydroxy, a $C_1$–$C_6$-alkoxy, $C_2$–$C_6$-alklanoyloxy group or a halo or $C_1$–$C_5$-alkanesulfonyloxy substituted $C_2$–$C_6$-alkanoyloxy group, with the proviso that $R_1$ can also be hydrogen and the groups $R_4$, $R_5$, and $R_6$ are the same or different and are hydrogen, halogen, trihalomethyl, $C_1$–$C_6$-alkyl, hydroxy, $C_1$–$C_6$-alkoxy, a $C_2$–$C_6$-alkanoyloxy group or a halo or $C_1$–$C_4$-alkanesulfonyloxy substituted $C_2$–$C_6$-alkanoyloxy group and X is the equivalent of a physiologically compatible anion and process of their production.

14 Claims, No Drawings

TUMOR RETARDING (1,2-DIPHENYL-ETHYLENEDIAMINE)-PLATINUM(II)-COMPLEXES

BACKGROUND OF THE INVENTION

There are known from German Offenlegungsschrift No. 3405611 antitumor active compounds. Thereby there are described (1,2-diphenyl-ethylenediamine)-platinum (II) complex compounds of the general formula

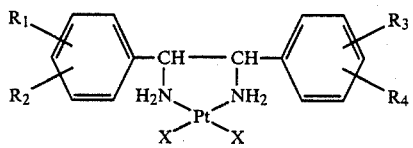

wherein the groups $R_1$, $R_2$, $R_3$, and $R_4$ are the same or different and are hydrogen, hydroxy groups, $C_1$–$C_6$-alkoxy groups, $C_2$–$C_6$-alkanoyl groups, optionally substituted by halogen atoms or $C_1$–$C_4$-alkanesulfonyloxy groups, or $C_3$–$C_6$-alkenoyloxy groups, wherein at least one of the groups $R_1$, $R_2$, $R_3$, or $R_4$ is not a hydrogen atom and x is the equivalent of a physiologically compatible anion.

SUMMARY OF THE INVENTION

The invention is directed to the subject matter defined in the claims.

There are prepared (1,2-diphenylethylenediamine)-platinum(II)-complexes of the general formula

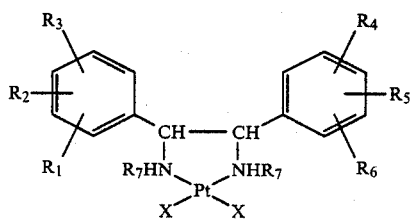

wherein $R_7$ is hydrogen or $C_1$–$C_6$ alkyl and $R_2$ is either (1) a halogen atom and the groups $R_1$, $R_3$, $R_4$, $R_5$, and $R_6$ are the same or different and are hydrogen, halogen, trihalomethyl, $C_1$–$C_6$-alkyl, hydroxy, $C_1$–$C_6$-alkoxy, a $C_2$–$C_6$-alkanoyloxy or a halo or $C_1$–$C_4$-alkanesulfonyloxy substituted $C_2$–$C_6$-alkanoyloxy group, or $R_2$ is (2) a hydroxy group, a $C_1$–$C_6$-alkoxy group, a $C_2$–$C_6$-alkanoyloxy group in the 4-position or a halo or $C_1$–$C_4$-alkaensulfonyloxy substituted $C_2$–$C_6$-alkanoyloxy group and if $R_2$ is (2) then the groups $R_1$ and $R_3$ which are the same or different are in the 2 and 6 positions of the phenyl group and are halogen, trihalomethyl, $C_1$–$C_6$-alkyl, hydroxy, a $C_1$–$C_6$-alkoxy, $C_2$–$C_6$-alkanoyloxy group or a halo or $C_1$–$C_4$-alkanesulfonyloxy substituted $C_2$–$C_6$-alkanoyloxy group, with the proviso that $R_1$ can also be hydrogen and the groups $R_4$, $R_5$ and $R_6$ are the same or different and are hydrogen, halogen, trihalomethyl, $C_1$–$C_6$-alkyl, hydroxy, $C_1$–$C_6$-alkoxy, $C_2$–$C_6$-alkanoyloxy group or a halo or $C_1$–$C_4$-alkaensylfonyloxy substituted $C_2$–$C_6$-alkanoyloxy group and X is the equivalent of a physiologically compatible anion.

The compounds are produced by reacting a tetrahalo-platinum (II) acid, a tetrahalo-platinum (II) complex salt having two monovalent cations or one divalent cation or a platinum (II) halide with compound of the formula

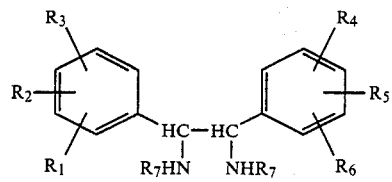

or an acid addition salt of compound II, wherein the groups $R_1$, $R_2$, $R_3$, $R_4$, $R_5$, and $R_6$ have the stated meanings, there are optionally introduced in free phenolic hydroxy groups a $C_2$–$C_6$-alkanoyl group optionally substituted by halogen or by $C_1$–$C_4$-alkanesulfonyloxy groups and optionally in a compound obtained of formula I the group X or the group X is exchanged for another physiologically compatible anion.

Medicines are prepared containing a compound of general formula (I) and in addition customary carriers and/or diluents or adjuvants.

A medicine can be produced by processing a compound of general formula I with customary pharmaceutical carriers or diluents or other adjuvants to pharmaceutical preparations or by bringing it into a therapeutically usable form.

The compounds of general formula I are used to produce medicines.

The compounds of the invention also can be administered to mammals, e.g. humans, dogs, cats, horses, and cattle in an amount effective to retard the growth of a tumor.

The new compounds of the invention have a decided antitumor activity together with good compatibility. The action is shown especially in the following animal and cell culture models:

Mouse leukemia P388, hormone independent human breast cancer cell line MDA-MB 231, hormone dependent human breast cancer cell line MCF7, hormone dependent mouse mammary carcinoma MXT, DMBA induced hormone dependent rat mammary carcinoma (DMBA is dimethylbenz[a]-anthracene).

The compounds of the invention prevent or retard both the growth of tumor cells present and also the formation of new tumor cells; furthermore they destroy tumor cells present or lead to their regression and prevent or weaken the formation of metastases.

In comparison to the known compounds the compounds of the invention have superior or more advantageous antitumor activity.

For example, the compounds of the invention wherein $R_2$ is a halogen atom have a better activity on hormone independent tumors, as for example on the mouse leukemia P388 and the hormone independent human mammary carcinoma cell line MDA-MB 231 than the previously known compounds.

The compounds of the invention wherein $R_2$ is hydroxy, $C_1$–$C_6$-alkoxy or $C_2$–$C_6$-alkanoyloxy have a specific effect on estrogen receptor-positive tumors, especially on the hormone dependent mouse mammary carcinoma MXT, the DMBA-induced hormone dependent rat mammary carcinoma and the hormone dependent human breast cancer cell line MCF7. This effect on the precedingly mentioned hormone dependent tumors is considerably greater than that of the known compounds.

Furthermore, these compounds of the invention of formula Ia below also have an effect on hormone independent tumors, for example on the mouse leukemia P388 and the hormone independent human breast cancer line MDA-MB 231 whereby this effect in comparison to that of the halogen comounds according to formula Ib below is markedly weaker.

The marked effect of the compounds of the invention wherein $R_2$ is hydroxy, $C_1-C_6$-alkoxy or $C_2-C_6$-alkanoyloxy (see for example formula Ia) an estrogen receptor-positive tumor (for example on horomone dependent mammary carinomas) depends on the following mechanisms.

1. They compete with endogenic (that is the body's own) estrogens in order to bind on estrogen receptors of the tumor cells. Through this they inhibit the tumor growth stimulating effect of the endogenic estrogens.

2. By binding the complex molecules to estrogen receptors the translocation into the cell nucleus of the tumor cell is made easier. By this process an enrichment is made possible which contributes to the specificity effect. The complex molecule binds if with splitting off of X-(leaving group) via the platinum atom on the DNA (desoxyribonucleic acid). Thereby the synthesis process occurring at the DNA (esecially the DNA synthesis) is blocked and consequently the growth of the tumor stopped.

Especially important compounds of the invention are within the following formula

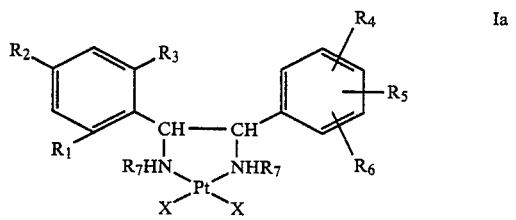

Ia

In this formula the individual groups $R_1$ to $R_7$ are defined as follows:

$R_2$ is OH, $C_1-C_6$-alkoxy (e.g. methoxy or ethoxy), a $C_2-C_6$-alkanoyloxy (e.g. acetoxy to hexanoyloxy) group, $C_2-C_6$-alkanoyloxy substituted by halogen (e.g. fluorine, bromine or chlorine) or by $C_1-C_4$-alkanesulfonyloxy;

$R_1$ and $R_3$ are halogen, trihalomethyl, $C_1-C_6$-alkyl, OH, $C_1-C_6$-alkoxy, a $C_2-C_6$-alkanoyloxy group, a $C_2-C_6$-alkanoyloxy group substituted by halogen or by $C_1-C_4$-alkanesulfonyloxy, with the proviso that $R_1$ can also be hydrogen if $R_3$ is halogen, trihalomethyl or $C_1-C_6$-alkyl;

$R_4$, $R_5$, and $R_6$ are hydrogen, halogen, trihalomethyl, $C_1-C_6$-alkyl, OH, $C_1-C_6$-alkoxy, a $C_2-c_6$-alkanoyloxy group, $C_2-C_6$-alkanoyloxy substituted by halogen or $C_1-C_4$-alkanesulfonyloxy; or example $R_4$ is a halogen atom (F, Cl, Br), preferably in the 4-position and $R_5$ and $R_6$ are hydrogen or $R_4$ has the same meanings as $R_2$ and is in the 4-position and $R_1$, $R_3$, $R_5$, and $R_6$ are halogen (preferably in each case in the 2 and 6 positions);

$R_7$ is H or $C_1-C_6$-alkyl.

In these compounds the meso form for example is especially strongly active.

Further important compounds of the invention are within the following formula Ib.

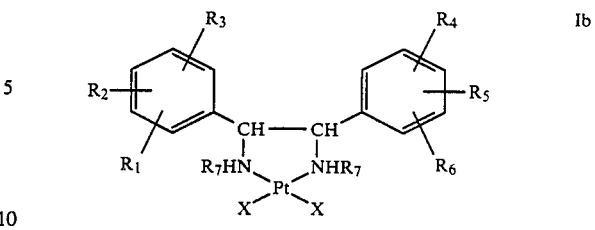

Ib

In formula Ib for example at least one of the groups $R_1$, $R_2$, and $R_3$ is a halogen atom (for example F, Cl, or Br, preferably in the 3 or 4 position L, the remaining groups $R_2$ and $R_3$ are the same or different and can be hydrogen or a halogen atom, while the groups $R_4$, $R_5$, and $R_6$ are the same or different and are either all hydrogen or likewise can be hydrogen and halogen (for example F, Cl, or Br), whereby the halogen atoms are preferably located in the 3 or 4 position and preferably at least one of the groups $R_4$, $R_5$ and $R_6$ is a halogen atom. Here also there especially are suitable compounds where the two phenyl rings are symmetrically substituted by the same substituents.

In these compounds generally the racemates are the most greatly effective.

The following data is directed to the preferred illustrations of the invention.

The $C_1-C_6$-alkyl groups, the alkoxy groups and the $C_2-C_6$-alkanoxyloxy groups can be straight or branched and preferably consist of 1 to 4 carbon atoms. As alkanoyloxy group there is especially preferred the acetoxy group. The alkanoyloxy groups can contain one or more (for example 1 to 6, especially 1 to 3) same or different halogen atoms. Especially there are located 1, 2, or 3 halogen atoms on one carbon atom, preferably on the α-C-atom. Furthermore the halogen atoms as well as the alkanesulfonyloxy group can be preferably located in the β-position of the alkanoyloxy group. For example there can be present the methane or ethanesulfonyloxy group. As halogen substituents there are preferably employed fluorine, chlorine and/or bromine. In regard to the trihalomethyl group trifluoromethyl is preferred.

The substituents $R_4$, $R_5$ and $R_6$ are preferably located in the 4 and/or 2 positions of the phenyl group. In case one of the groups $R_4$, $R_5$, or $R_6$ is hydrogen the 2 other substituents preferably also are located in 2,4-position of the phenyl group.

In case one or more of the groups $R_1$, $R_3$, $R_4$, $R_5$, $R_6$ or $R_7$ is an alkyl group, preferably it is a methyl group, an ethyl group, an isopropyl group or a butyl group.

The meaning of $R_7$ on the two nitrogen atoms of the five member platinum containing rings can be identical; however, it is also possible that $R_7$ on one nitrogen atom is hydrogen and on the other N-atom is a $C_1-C_6$-alkyl group.

Especially favorable activity is possessed for example by those compounds of formula I wherein $R_2$ is as defined above and $R_1$ and $R_3$ are the same or different and are chlorine, fluorine, bromine, iodine, trifluoromethyl, methyl, ethyl, propyl, isopropyl, butyl, isobutyl, or tert.butyl, whereby one of the groups $R_1$ and $R_3$ or both groups also can be hydrogen and the phenyl group having the substitutents $R_4$, $R_5$, and $R_6$ is substituted in the same manner (symmetrical substitution to the phenyl group with the group $R_1$, $R_2$, and $R_3$). Furthermore, those compounds are important where $R_2$ is as defined above and the groups $R_1$ and $R_3$ have the previously stated meanings and the right phenyl group is then unsymmetrical to the phenyl group having the substituents $R_1$, $R_2$, and $R_3$ and $R_4$, $R_5$, and $R_6$ are within the scope of the stated definitions. Preferably $R_4$, $R_5$ and $R_6$ in this case are hydroxy, halogen or hydrogen, whereby at least one of the substituents $R_4$, $R_5$ or $R_6$ is halogen or hydroxy and the remaining two other substituents are hydrogen.

The group X represents the known and customary physiologically compatible and pharmaceutically usable anions of mono or polyvalent acids. For example, especially there are used the anions of the following acids:

HBr, HCl, HI, HF, $HNO_3$, $H_2SO_4$ ($SO_4^{--}$); $H_3PO_4$ ($HPO_4^{--}$); $H_2CO_3$, ($CO_3^{--}$); camphorsulfonic acid, aliphatic or aromatic sulfonic acids, for example $C_1$–$C_6$-alkylsulfonic acids (for example methanesulfonic acid, ethane-, propane- or hexanesulfonic acid), benzene- or naphthalenesulfonic acid, which optionally are substituted once or twice by methyl groups (toluenesulfonic acid, especially o- or p-toluenesulfonic acid); aliphatic $C_1$–$C_4$-monocarboxylic acid, which optionally are substitued once, twice, or three times by halogen atoms (especially Cl,F) (for example formic acid, acetic acid, propionic acid, chloroacetic acid, dichloroacetic acid, trifluoroacetic acid, trichloroacetic acid); aliphatic $C_2$–$C_{11}$ dicarboxylic acids, which optionally contain a double bond (for example oxalic acid, malonic acid, 2-aminomalonic acid, malonic acid which is substituted in the 2-position by a benzyl group or one or two $C_1$–$C_4$-alkyl groups, maleic acid, fumaric acid, succinic acid); aliphatic monohydroxy- and dihydroxy-monocarboxylic acids having 2 to 6, especially 2 to 3 carbon atoms, in which case they are preferably α-monohydroxycarboxylic acids such as lactic acid, glyceric acid, or glycolic acid, aliphatic monohydroxy- and dihydroxy-, di- and carboxylic acids having 3 to 8 carbon atoms, especially 3 to 6 carbon atoms, such as malic acid, tartaric acid, malonic acid which is substituted on the middle carbon atom by a hydroxy group and optionally can be substituted by a $C_1$–$C_4$-alkyl group, isocitirc acid or citric acid, phthalic acid which optionally is substituted by a carboxy group (especially in the 4-position); gluconic acid; glucuronic acid; the natural α-aminoacids (for example L-aspartic acid); 1,1-cyclobutanedicarboxylic acid; organophosphoric acids, such as aldose and ketose phosphoric acids, (for example the corresponding mono- and diphosphoric acids) for example aldose-6-phosphoric acids such as D-orL-glucose-6-phosphoric acid, α-D-glucose-1-phosphoric acid, D-fructose-6-phosphoric acid, D-galactose-6-phosphoric acid, D-ribose-5-phosphoric acid, D-fructose-1,6-diphosphoric acid; glycerine phosphoric acids (whereby the phosphoric acid residue is connected on one of the end or on the middle glycerine oxygen atom) such as α-D,L-glycerine phosphoric acid, '-glycerine phosphoric acid, N-phosphone-acetyl-aspartic acid.

As acids for the anion X additionally there can be used aromatic carboxylic acids which contain one or more carboxy groups as well as additionally $C_1$–$C_4$-alkoxy groups and/or hydroxy groups and/or hydroxy groups. In case several carboxy groups are located on the aromatic radical (for example a benzene ring), preferably at least 2 carboxy groups are in adjacent position. In case the benzene ring for example contains 4 or 5 carboxy groups, complexes can form, which contain per mole of the benzenecarboxylic acid anions 2 moles of the platinum component. 2 adjacent carboxy groups neutralize at the same time 1 mole of the platinum component, so that for example, in the case of benzenepentacarboxylic acid the 1 and 2 position as well as the 4 and 5 position carboxy groups at the same time saturate 1 mole of the platinum component (thus together 2 moles), while the free carboxy group in the 3 position is free or in the salt form with a physiologically compatible cation (for example alkali cation, especially sodium cation).

This is generally true if the anions X still have additional acid functions which are not used for saturation of the platinum. The analogy is true in the case of benzenehexacarboxylic acid, in which case here optionally 1 mole of this acid can saturate 3 moles of the platinum component.

Examples of such acids are benzene monocarboxylic acid, benzene dicarboxylic acids, benzene tricarboxylic acids, (for example trimellitic acid), benzene tetracarboxylic acid, benzene pentacarboxylic acid, benzene hexacarboxylic acid, syringic acid, orotic acid. Likewise, there can be used as acids which form the anions X aminoacids or aminoacid derivatives whose basic amino group is neutralized by an acid group. Thereby there can be used for examples aminoacids of the following structure:

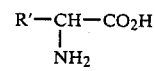

wherein R' is hydrogen, a phenyl radical, an indolyl-(3)-methyl radical, imidazolyl-(4)-methyl radical, a $C_1$–$C_{10}$-alkyl group or a $C_1$–$C_{10}$-alkyl group which is substituted by a hydroxy group, a carboxy group, a $C_1$–$C_6$-alkoxy group a mercapto group, a $C_1$–$C_6$-alkylthio group, a phenyl group, a hydroxyphenyl group, a $C_2$–$C_6$-alkylamio group or a $C_1$–$C_6$-alkoxycarbonyl group.

The basic amino group in the 2 -position hereby is neutralized (acylated) by a customary aminoacid protective group, for example by a $C_2$–$C_6$-alkanoyl radical or the butyloxycarbonyl radical.

In case in the above formula R' is an alkyl group it is preferably a $C_1$–$C_6$-alkyl group which for example contains in the 2-, 3-, 4-, 5-, or 6-position (counting begins at the position of connection of the alkyl group to the rest of the molecule) a $C_2$–$C_6$-alkanoylamino group, an imidazolyl-(4)-methyl radical or an indolyl-(3)-methyl radical. Individual examples of such aminoacids are leucine (preferably D- and L-form), valine (preferably D- and L-form), phenylalanine (preferably D-and L-form), phenylglycine (preferably D-and L-form), alanine (preferably D-and L-form), isoleucine (preferably D- and L-form), asparagine (preferably D- and L-form), lysine (preferably D- and L-form), tryptophane (preferably D- and L-form), tyrosine (preferably D- and L-form), ornithine (preferably D- and L-form).

Thereby the basic amino groups are blocked by a customary acylamino protective group, especially by the acetyl group or the butyloxycarbonyl group.

Formula I also embraces the possible enantiomers and diastereomers. In case the compounds are racemates these can be resolved in known manner, for example by means of an optically active acid into the optically active isomers. However, it is also possible from the outset to employ enantiomers or optionally also diastereomeric starting materials, in which case as end product there is obtained a corresponding pure optically active or diastereomeric compound. Independent of the structure of the radical X the 1,2-diphenyl ethylenediamine portion has 2 asymmetric carbon atoms and therefore can be present in the racemate form or in the levorotatory or dextrorotatory or in the meso form. Additionally forms can arise through different enantiomeric or diastereomeric forms of the radical X. Especially favorable activities are found when the two asymmetric centers of the 1,2-dipheyl-ethylenediamine portion have the same configuration. dependent of the geometry of the platinum atom the compounds of the invention of formula I always are the cis-compounds.

The starting amine II is employed for example as the racemate, as meso compound, as pure dextrorotatory or levorotory form or in another diastereomeric form.

This configuration remains in the production of the platinum complex.

The process for the production of compounds I of the invention is carried out in a solvent at temperatures between 0° and 90° C., preferably 10° to 60° C., especially 20° to 50° C. As solvents there can be used for example water, $C_1$-$C_6$-alkanols (methanol, ethanol, tert.butanol), tetrahydrofuran, dioxan, dimethylsulfoxide, dimethylformamide, ethyleneglycoldimethylether, diethyleneglycoldimethylether as well as mixture of the solvents, especially mixtures with water.

The two reactants (platinum compound and compound II) are preferably employed in equimolar amounts. The pH of the reaction solution should be between 5 and 7, preferably at 6. The regulation of the pH is carried out especially by addition of alkali, preferably aqueous sodium hydroxide or potassium hydroxide or for example also by means of sodium carbonate.

As tetrahalogen-platinum (II) compounds (acids as well as complex salts) there are employed the corresponding tetrachloro-, tetrabromo-, and tetraiodo compounds. In the event platinum (II) halide is employed as starting component the same halogen atoms are used.

As monovalent cations there are used alkali ions, especially sodium and potassium; however, there can also be used lithium, rubidium, cesium, likewise $NH_4^+$, $NR_4^+$, $PR_4^+$, or $AsR_4^+$ in which R is a $C_1$-$C_6$-alkyl radical or a phenyl radical. Divalent cations can be alkaline earth ions, especially $Mg^{2+}$ and $Ca^{2+}$, as well as $Zn^{2+}$. As platinum (II) halides there can be used for example $PtCl_2$, $PtBr_2$, and $PtI_2$.

The compound II is employed either in the form of the diamine or in the form of an acid addition salt: for example, as the monohydrochloride or dihydrochloride, mono- or dihydrobromide mono- or dihydroiodide or as the salt with another customary acid. Especially there can be used acids whose anions form the radical X. Furthermore, the diamine can be employed in the form of the acetate or diacetate, in which case optionally before mxing the reactants there is added potassium chloride (for example 2 moles per mole of compound II). Likewise the diamine II can be employed in the form of the carbonate.

In compounds of formula I free phenolic hydroxy groups present can be acylated by $C_1$-$C_6$-alkanoyl groups. These alkanoyl groups can contain halogen atoms (for example Cl, Br) or $C_1$-$C_4$-alkanesulfonyloxy groups. This acylation can be carried out for example by means of $C_1$-$C_6$-alkanoyl halides or the anhydrides of saturated aliphatic $C_1$-$C_6$ monocarboxylic acids at temperatures between 10° and 80° C., especially 20°-30° C. in the presence of customary acid binding materials.

The alkanoyl halide or anhydride optionally can contain at least 1 halogen atom or at least one $C_1$-$C_4$-alkanesulfonyloxy gruop. Especially there can be used as acid binding materials aliphatic tertiary amines such as for example diisopropyl ethyl amine. As inert solvent or suspension agents for the acylation there can be used for example lower aliphatic halohydrocarbons (chloroform), aprotic solvents such as amide, $C_1$-$C_4$-alkylamides and $C_1$-$C_4$-dialkylamides of aliphatic $C_1$-$C_4$-carboxylic acids (dimethyl formamide, dimethyl acetamide), N-methyl-pyrrolidone, dimethyl sulfoxide or mixture of these agents.

However, the acylation can also be carried out in a two phase system, for example water/chloroform, in which the case the acylated platinum (II) complex is located generally in the water phase and the mixture of acid chloride and tertiary amine (diisopropyl ethyl amine) is found in the chloroform phase. The acylated platinum (II)-complex by addition of a corresponding anion can be converted into a less water soluble, desired complex and can be isolated by filtration. This is especially true if the acylated dihydroxo-platinum (II) complex is present in the water phase. In general it is suitable with the acylation in a two phase system to exchange the anion X of the platinum complex of formula I for OH— before the acylation by means of anion exchanger since the corresponding dihydroxoplatinum (II) complex has good water solubility. As acid halides there are preferably employed the corresponding chlorine, bromide, and in a given case, the iodide. As anhydride of $C_1$-$C_6$-carboxylic acids there are especially employed the symmetrical acid anhydrides.

The exchange of the ligands X against other ligands for example can be carried out by means of silver halide precipitation. For this purpose for example a dihalo-(1,2-diphenyl)ethylenediamine-platinum-(II)-compound of formula I, wherein X is halogen (chlorine, bromine, or iodine) is reacted in a solvent or suspension agent at temperatures between 0° and 90° C., preferably 10° to 50° C., especially 15° to 25° C., with the silver salt of another acid, which corresponds to the definition of X. However, thereby there can also be used as the silver salt silver nitrate (for example aqueous silver nitrate solution) and there is obtained an ionic diaquo complex of the formula.

The weakly bound ligand water is readily replaced from this complex by affiniated anions (for example $Cl^-$, $Br^-$ in the form of NaCl, KCl, NaBr, KBr, malonate$^{2-}$, chloroacetate$^-$, oxalate$^{2-}$ 1,1-cyclobutanecarboxylic acid anion$^{2-}$ as well as the rest of the stated acid radicals X used in the form of acids or their salts, expecially their alkali salts, (e.g. sodium or potassium salts.

The same compounds can also be obtained by reaction of equimolar amounts of HX and nitrate free platinum complex (the latter using anion exchangers in the hydroxide form, for example Dowex 1-8X).

An exchange of the group going off (for example $SO_4^{2-}$ or oxalate anion$^{2-}$) is also possible in the case of the sulfate or oxalato-(1,2-diphenyl-ethylenediamine)-platinum (I) compounds by reaction with alkaline earth salts (e.g. calcium salts) which contain the desired X-ligands (for example glyeric acid), insofar as the complex formed is water soluble and therewith permits the separation of the badly water soluble alkaline earth sulfate or oxalate.

Suitable X-ligands for this process are preferably the anions of hydroxycarboxylic acids, sulfonic acids, haloacetic acids, nitric acid.

The solvent or suspension agents which have been given for the process of production of the compounds I also can be used for the exchange reaction (especially suited are water and diemethyl formamide as well as also methanol, ethanol, tert.butanol). The exchange reaction is carried out for example in the pH range between 3 and 7.

Production of Unknown Starting Materials of Formula II

The production of 1,2-dialylethylenediamines having symmetrically substituted phenyl groups of Formula II insofar as they are not described.

For this purpose reference is made to the following literature: Journal of Medicinal Chemistry, 1982, Volume 25, pages 1374–1377; Chemische Berichte 1976, Volume 109, page 1.

A. General Directions of the Ether Cleavage With BBr$_3$ For The Production of Hydroxy Substituted Meso and d,l-1,2-Diarylethylenediamines of Formula II 5.5 mmoles of the methoxy substituted meso, respectively d,l-1,2-diarylethylene-diamine specified were dissolved in 150 ml of water-free CH$_2$Cl$_2$ and cooled to −50° C. There were added under a nitrogen atmosphere 22 mmoles of boron tribromide and the mixture stirred for 30 minutes at this temperature. After stirring for a further 18 hours at room temperature the excess BBr$_3$ was carefully hydrolyzed with methanol under cooling with ice. After removal of the solvent residue was taken up in 50 ml of water and the pH adjusted to 7 with saturated NaHCO$_3$ solution. The precipitate was filtered off with suction, washed with water, ethanol and CH$_2$Cl$_2$ and dried over P$_2$O$_5$. As a rule there were obtained analytically pure products. For example the starting amines for examples 2, 4, 10, 12, 16, 20, 21, and 24 were obtained in this manner.

The cleavage of the ether also can be carried out with hydrobromic acid according to the following procedure:

0.01 mole of the methoxy substituted meso-1,2-diarylethylenediamine was heated under reflux in 60 ml of 47% HBr for 24–48 hours. After cooling the precipitate was filtered off with suction, washed with very little amounts of ice water and dissolved in hot water. The solution was treated with 20% NaOH solution until the precipitated ethylenediamine again went into solution as phenolate. After filtering the pH was adjusted to 7 with 2N HCl and the precipitate filtered off with suction. The product was washed with water and ethanol and the product which was analytically pure for the most part was dried over P$_2$O$_5$.

For example the starting amines for examples 6, 8, 14 and 18 were obtained in this manner.

B. General Directions for the Production of the Meso Configurated 1,2-Diarylethylenediamine of Formula II via the Meso→Meso-Diaza-Cope Rearrangement 0.5 mole of N,N'-disalicylidene-meso-1,2-diarylethylenediamine was suspended in 200 ml of 1N H$_2$SO$_4$, respectively 30–40% H$_2$SO$_4$. The salicylicaldehyde set free by hydrolysis was removed from the reaction mixture by means of steam distillation. When aldehyde can no longer be detected in the distillate the reaction solution was filtered hot and after cooling carefully adjusted to pH 11–12 with 20% NaOH solution. The precipitate was extracted with CH$_2$Cl$_2$. The combined extracts were washed with water and dried over MgSO$_4$. The solution was concentrated until the product began to precipitate. There was then added about 100 ml of ether and the mixture allowed to crystallize in the refrigerator. The ethylenediamine was filtered off with suction, washed with ether and recrystallized in ethanol.

The production of the corresponding N,N'-disalicylidene-meso-1,2-diaryl-ethylenediamine (Diaza-Cope-Rearrangement) for example can be carried out in the following manner: meso-1,2-bis-(2-hydroxyphenyl)-ethylenediame was heated under reflux with 2 molar equivalents of the corresponding benzaldehyde of the formula

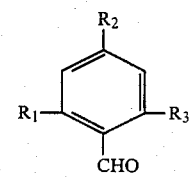

in acetonitrile. The suspension was stirred continuously and heated to boiling until were formed homogeneous, yellow cubes (about 4–5 hours). After distilling off half of the solvent and cooling to room temperature the precipitate was filtered off with suction, washed with a little acetonitrile and dried in a vacuum desicator over P$_2$O$_5$.

For examples 15 and 16 the corresponding mixture in toluene was heated under reflux on the water separator for 24 hours. There can only be isolated a mixture of N,N'-disalicylidene-meso-1,2-bis (2,6-dimethyl-4-methoxy-phenyl)ethylenediamine and the not rearranged diimine N,N'-bis(2,6-dimethyl-4-methoxybenzylidene-meso-1,2-bis(2-hydroxyphenyl)ethylenediamine which can be reacted further without additional separation.

C. General Directions for the Synthesis of d,l-Configurated 1,2-Diarylethylenediamine of formula II via the Degenerated Diaza-Cope-Rearrangement 0.1 mole of the N,N'-dibenzylidene-meso-1,2-diarylethylenediamine specified in a 1 liter, three-necked flask is held under stirring in an oil bath at its melting temperature until the crystal mass is completely melted. After cooling to about 80° C. there is added 250 ml of 2N H$_2$SO$_4$ and the suspension is subjected to a steam distillation until no more aldehyde passes over. The clear solution is filtered hot and allowed to stand overnight for crystallization at room temperature. the crystalline dihydrosulfate of the racemic 1,2-diarylethylenediamine is filtered off and then washed with a little amount of ice cold 2N H$_2$SO$_4$. Subsequently it is covered in a separatory funnel with 2N NaOH solution and extracted with CH$_2$Cl$_2$. After drying over MgSO$_4$ the solvent is rotated off and the oily residue recrystallized in ethanol. With products that crystallize with difficulty the dehydrochloride can be precipitated with ethereal HCl. The filtrate contains the dihydrosulfate of the meso-configurated 1,2-diaryletheylenediamine, which can be isolated analogous to Method B.

For example the starting amines for the complexes of Examples 3 and 4 were obtained in this manner.

The N,N'-dibenzylidene-meso-1,2-diarylethylenediamine used hereby can be obtained for example as follows:

The meso-1,2-diarylethylenediamine in each case is dissolved in acetonitrile and after addition of 2 molar equivalents of the corresponding benzaldehyde as stated under B, is heated under reflux for 3 hours. The mixture is allowed to cool, filtered with suction on a Buchner funnel and post washed with some acetonitrile and acetone and dried in a desiccator over $P_2O_5$.

D. General Direction for the Production of d,l-Configured 1,2-Diarylethylenediamine via the d,l→d,l-Diaza-Cope-Rearrangement 25 mmoles of d,l-1,2-bis(4-methoxyphenyl)-ethylenediamine were dissolved in 250 ml of methanol and added to 50 mmoles of the corresponding benzaldehyde dissolved in methanol as stated under B. The solution is heated under reflux for 24 hours and subsequently the solvent rotated off. The oily residue can be separated by column chromatography over silica gel 60. The diimine mixture hydrolyzes for the most part on the column and by suitable selection and sequence there can be isolated from the solvent mixture isomer free d,l-product. After addition of ethereal HCl to the ethanolic solution there can be obtained the d,l-1,2-diarylethylenediamine in crystalline form as the dihydrochloride. The starting amine for the compound according to Example 19 for example can be obtained according to this method.

E. General Direction for the Production of N,N'-Dialkylated 1,2-Diarylethylenediamine by Reductive Dimerization of the Corresponding Benzaldehyde Alkylimine with Tetraphenylethanediol A mixture of 0.4 mole of benzaldehydealkylimine of the formula

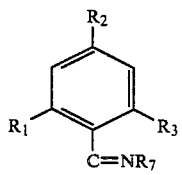

and 0.4 mole of 1,1,2,2-tetraphenylethanediol in 200 ml of 2-propanol was heated for 24 hours under reflux. After cooling the precipitate (meso-isomer) was filtered off with suction, dissolved in $CH_2Cl_2$ and extracted with 2N HCl. The aqueous phase was made alkaline with 2N NaOH and extracted with $CH_2Cl_2$. The organic phase was washed with water and dried over $MgSO_4$. After rotating off the solvent there was obtained the meso product in crystalline form, which was recrystallized in ethanol. The filtrate of the reaction mixture was rotated off and the remaining brown oil column chromatographed over silica gel 60. The isomer free d,l-product was obtained by successive elution with $CH_2Cl_2$, ether and methanol and can be recrystallized in acetonitrile.

The production of the benzaldehyde alkylimine was carried out from the corresponding substituted benzaldehydes and the alkylamine $NH_2R_7$ in the customary for example in chloroform, first at room temperature (2 hours stirring) and subsequently heating under reflux (30 minutes).

In the following there is given the directions for the production of various benzaldehydes which have not been previously described, which were employed as starting aldehydes in the above stated methods for the production of amine II. Other benzaldehydes which were not previously known can be obtained in analogous manner.

DETAILED DESCRIPTION

2-Iodo-4-Methoxy-Benzaldehyde 0.1 mole of 4-methoxybenzaldehyde dimethylacetal was treated in a flame dried flask under a $N_2$-atmosphere with 500 ml of water-free ether and cooled to $-60°$ C. in dry ice-acetone-bath. With the help of a long, flexible steel needle 0.11 mole of a solution of tertiary butyl lithium in hexane was driven out of the supply flask through a serum cap under nitrogen. The color suddenly changed to yellow. The temperature was allowed to increase to $-25°$ C. and stirring continued for another 3 hours until a yellow, voluminous precipitate had formed. The 2-lithium-4-methoxy-benzaldehyde dimethyl acetal thus obtained was treated immediately dropwise at $-25°$ C. with 0.11 mole of $I_2$, dissolved in 200 ml of water-free ether. The remaining of the iodine color showed the end of the reaction. The solution was stirred for a further 30 minutes at room temperature and subsequently treated with water. The product was extracted with ether, washed successively with aqueous $Na_2SO_3$ solution, 2N HCl solution, saturated $NaHCO_3$ solution and water and dried over $MgSO_4$. The solvent was rotated off and the residue recrystallized in methanol. Colorless needles, M.P. 109°-111° C.

2-Bromo-4-Methoxybenzaldehyde 2-lithium-4-methoxybenzaldehyde dimethyl acetal was treated quickly with 0.11 mole of bromine at $-60°$ C. Subsequently stirring was carried out at room temperature for 1 hour. The product was treated with water, extracted with ether and washed successively with aqueous $Na_2SO_3$ solution, 2N HCl solution, saturated $NaHCO_3$ solution and water. After drying over $MgSO_4$ and rotating off the ether there remained a red-brown oil, which was subjected to a steam distillation. The distillate was extracted with $CH_2Cl_2$, dried over $MgSO_4$ and concentrated. The residue was column chromatographed over silica gel 60 (Merck Co., Darmstadt) with ether/petroleum ether 40-60 1:2 ($R_f \sim 0.5$–$0.6$). Colorless, long needles, M.P. 73°-74° C.

2-Fluoro-4-Methoxy-Benzaldehyde

By reacting 3-fluoroanisole with bromine in the presence of iron powder in $CHCl_3$ at $-60°$ C. in a dry ice-acetone-bath in manner analogous to that of Quelet, R; Paty M in Process Verbauz soc. sci. phys et nat. Bordeaux 1944–1945, 19, there was obtained after fractional distillation under a water jet vacuum an isomeric mixture of 4-bromo-3-fluoroanisole and 2-bromo-5-fluoroanisole, which was further worked up without separation. Colorless liquid, Boiling point 93°-95° C./144 Torr.

0.1 mole of n-butyl lithium-hexane solution was treated in a nitrogen atmosphere with 150 ml of water-free ether and cooled to $-70°$ C. 0.1 mole of the isomeric mixture described above was taken up in 50 ml of water-free ethanol and dropped in with such a velocity that the reaction temperature did not exceed $-55°$ C. Stirring was continued at this temperature for further 15 minutes and then mixture was treated with N-formylpiperidine dissolved in 25 ml of water-free either whereby the temperature was held again below −55° C. In the event that the following test for metal-organic compound with Michler's ketone is negative, the mixture was brought to room temperature, acidified with 2N HCl and the organic phase separated off. The ether phase was washed with saturated NaHCO3 solution and water, dried ove MgSO4 and the solvent drawn off. The oily residue was chromatographed over silica gel 60 with CH2Cl2/petroleum ether 40-60 1:1 ($R_f \sim 0.45$–0.5). Colorless needles M.P. 42.5°–44° C.

Analogously there was obtained 4-methoxy-2-trifluoromethyl benzaldehyde (M.P. 38°−39° C. after purification by column chromatography over silica gel with ether/petroleum ether) via a mixture of 4-bromo-3-trifluoromethyl anisole (boiling point 46°-47° C./0.6 Torr). Carrying out the bromination: 18 hours at room temperature.

2-6-Dichloro-4-Methoxybenzaldehyde 1-mole of precipitated activated manganese dioxide and 800 ml of benzene were heated for 2 hours at boiling on the water separator. Subsequently there was added 0.2 mole of 2,6-dichloro-4-methoxybenzyl alcohol and the mixture heated under reflux overnight again on the water separator. After cooling to room temperature the manganese dioxide was filtered off with suction over a glass funnel and washed with benzene. After rotating off the solvent there was obtained generally a very pure product, which as occasion demands, can be recrystallized from methanol, however, with great loss of yield.

The 2,6-dichloro-4-methoxybenzyl alcohol employed was obtained as follows:

0.56 mole of 3,5-dichloroanisole was stirred with 30.3 grams of paraformaldehyde in 1.5 liters of concentration HCl and 15 ml of concentrated H2SO4 for 7 hours at 60° C. reaction temperature. After cooling the phases were separated, the aqueous layer extracted with CH2Cl2 and the combined organic layer washed with water. After drying over MgSO4 and rotating off the solvent there remained a colorless oil. To this oil were added 530 ml of 2N NaOH solution, 530 ml of water and 530 ml of dioxane and the mixture heated to boiling for 3 hours. The organic phase has separated off after cooling, the aqueous phase was shaken with CH2Cl2 and subsequently the combined organic phases washed with water and dried over MgSO4. After rotating off the solvent the oily residue was treated with 100 ml of CHCl3 and the precipitate which formed was filtered off. The chloroform was rotated off and the oily residue separated by column chromatography over silica gel 60 with a 1:1 mixture of petroleum ether 40-60/ether. Colorless needles, M.P. 78°–79° C.

2-Chloro-4-Methoxybenzaldehyde

To 0.1 mole of 2-lithium-4-methoxybenzaldehyde dimethyl acetal 0.11 mole of benzenesulfonyl chloride dissolved in 50 ml of anhydrous ether were added by means of a syringe at −60° C. Subsequently stirring was carried out at room temperature for 1 hour. The white precipitate which formed was dissolved again by addition of ice water. The product was extracted with either, washed with 2N HCl solution, saturated NaHCO3 solution and water, dried over MgSO4 and evaporated. The residue was separated by column chromatography over silica gel 60 (Merck Co., Darmstadt) with ether/petroleum ether 40-60 1:2. $R_f$ 0.75-0.8. Colorless needles, M.P. 60°-61° C.

The compounds of the invention exhibit a good antitumor activity on the human MDA-MB 231 breast cancer cell line (Dissertation Jennerwein, University of Regensburg, 1985, page 151), on the leukemia P388 (mouse) (see Dissertation Johann F. -X, Karl, University of Regensburg, 1985, pages (8,81–86), on the DMBA-induced mammary tumor of the rat 99–102 on the MCF 7-breast cancer line of humans, 88–89 and on the MXT mammary carcinoma (mouse) (93, 94).

For example on the mammary cancer of the rat, which was induced by 7, 12-dimethylbenz [a]-anthracene (DMBA), with the compound of Example 18 at a dosage of 3×6.5 mg/kg body weight/week there was determined with 88% of the tumors a complete remission. In the testing on the hormone independent human mammary tumor cell line MDA-MB 231 the compounds of the invention show for example in vitro in concentrations between $10^{-5}$ and $10^{-7}$ moles/liter a 50% inhibition of the growth of this cell line. The inhibition of [$^3$H]-thymidine incorporation is of the same order of magnitude. The compounds of the invention act on the lymphocytic leukemia P388 (mouse) for example in dosages between 10 and 50 mg/kg (intraperitoneal application).

The orientation of the effect of the compounds of the invention is comparable with that of the known medicine cisplatin.

The lowest dosage leading to 65% complete remission in the above mentioned animal experiment is 3×3.25 mg/kg/week subcutaneously.

As a geneal dosage for the activity (animal experiments as above) there are used for example:
5–20 mg/kg orally, especially 10 mg,
1–10 mg/kg intravenously, especially 6.5 mg, Indications for which the compounds of the invention can be considered for treatment include tumor illnesses, especially mammary, endometrium carcinoma, cervical carcinoma, ovarial carcinoma and prostate carcinoma, as well as leukemia, hodenteratoma and bladder carcinoma.

The pharmaceutical preparations generally contain between 100 to 200, preferably 150 mg of the active components of the invention.

The dispensation for example can be carried out in the form of tablets, capsules, pills, dragess, plugs, salves, jellies, creams, powders, dusts, aerosols, or in liquid form. As liquid forms of use there can be employed: oily or alcoholic respectively aqueous solutions as well as suspensions and emulsions. Preferred forms of use are tablets which contain between 100 and 200 mg or solutions which contain between 0.02 to 0.04% of active material.

The individual dosage of the active components of the invention for example can be:
(a) with oral forms of the medicine between 100 to 200 mg, preferably 150 mg;
(b) with parenteral forms of the medicine (for example intravenously, intramuscularly), between 100 and 200 mg/m² body surface area, preferably 150 mg/m² body surface are:
(c) with forms of medicine for rectal or vaginal application between 1 to 5%, preferably 2.5%,
(d) with forms of the medicine for local application to the skin and mucosa (for example in the form of solutions, lotions emulsions, salves, etc.) between 1 to 5%, preferably 2.5%.

(The dosages in each case are based on the free base.)

For example, there can be recommended 3 times daily 1 to 4 tablets having a content of 100 to 200 mg of active material or for example with intravenous injection 1000 ml having an active material content corresponding to 100 to 200 mg/m² body surface area. With oral dispensation the minimum daily dosage for example is 300 mg; the maximum daily dosage with oral dispensation should not exceed 800 mg.

The acute toxicity of the compounds of the invention on the mouse (expressed by the $LD_{50}$ mg/kg; method of Miller and Tainter; Proc. Soc. Exper. Biol. a Med. 57 (1944) 261) for example with intraperitoneal application above 100 mg/kg, frequently above 1000 mg/kg.

The medicine can used in human medicine and in verterinary medicine alone or in admixture with other pharmacologically active materials.

The composition can comprise, consist essentially of, or consist of the stated materials and the processes can comprise, consist essentially of, or consist of the recited steps with such materials.

EXAMPLES

Examples 1–24 are set forth in Table 1. The physical properties of the platinum (II) complexes are given in Table 2. Examples 1–24 are directed to the production of platinum (II) complexes of the invention of the following formula

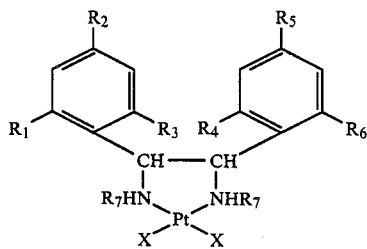

All of the complexes of Examples 1–24 are pale yellow to yellow powders.

General Directions for the Production of Platinum Complexes in Aqueous Medium 1 mmode of 1,2-diarylethylenediame is suspended in 20 ml of distilled water and dissolved by the addition of 2 ml of 2N HCl. The filtered solution is treated with 20 ml of tertiary-butanol and heated to 40° C. Slowly with stirring there is dropped in 0.5N NaOH until the free base begins to precipitate (pH noted). There is subsequently added to the solution dropwise 415 mg (1 mmole) of $K_2PtCl_4$ dissolved in 10 ml of water. Stirring is carried out at 40° C. with the exclusion of light and the pH adjusted at intervals of 4–5 hours to the noted pH value. A constant pH over a long time indicates the end of the reaction. After cooling to room temperature the yellow, generally analytically pure precipitate is drawn off with suction via a frit (G-4), washed successively with 2N HCl and water and dried in a drying pistol at 100° C. over $P_2O_5$. In the event it is necessary the complex is dissolved in a little amount of dimethylformamide for purification and precipitated with 5% NaCl solution.

The complexes of Examples 1–15, 17–21, and 23–24 were produced according to this method.

General Directions for the Production of the Platinum Complexes in Organic Medium 1 mmole of the 1,2-diarylethylenediamine is dissolved or suspended in 20 ml of dimethylformamide and treated with 1 mmole of $K_2PtCl_4$ dissolved in 5 of $H_2O$/dimethylformamide (1:1 mixture). The mixture is stirred in the dark at room temperature until a red to yellow colored precipitate results. If no color change is noticable after 3 days then there is added 1 ml of dimethyl sulfoxide and the solution stirred for a further 3–4 hours. The yellow solution is subsequently evaporated to dryness in a high vacuum. There was added to the yellow, oily residue 50 ml of 5% NaCl solution and the mixture stirred for 6 hours. The yellow, finely crystalline precipitate is filtered off with suction, washed with 2N HCl and water and dried over $P_2O_5$ in the drying pistol at 100° C.

The complexes according to Examples 16 and 22 were produced by this method.

TABLE 1

| Ex. No. | $R_1,R_4$ | $R_2,R_5$ | $R_3,R_6$ | $R_7$ (both) | X | Configuration | Color |
|---|---|---|---|---|---|---|---|
| 1 | $CH_3$ | $OCH_3$ | H | H | Cl | meso | pale yellow powder |
| 2 | $CH_3$ | OH | H | H | Cl | meso | pale yellow powder |
| 3 | $CH_3$ | $OCH_3$ | H | H | Cl | d,l | pale yellow powder |
| 4 | $CH_3$ | OH | H | H | Cl | d,l | pale yellow powder |
| 5 | I | $OCH_3$ | H | H | Cl | meso | yellow powder |
| 6 | I | OH | H | H | Cl | meso | light yellow powder |
| 7 | Br | $OCH_3$ | H | H | Cl | meso | light yellow powder |
| 8 | Br | OH | H | H | Cl | meso | light yellow powder |
| 9 | Cl | $OCH_3$ | H | H | Cl | meso | light yellow powder |
| 10 | Cl | OH | H | H | Cl | meso | light yellow powder |
| 11 | F | $OCH_3$ | H | H | Cl | meso | light yellow powder |
| 12 | F | OH | H | H | Cl | meso | light yellow powder |
| 13 | $CF_3$ | $OCH_3$ | H | H | Cl | meso | yellow powder |
| 14 | $CF_3$ | OH | H | H | Cl | meso | yellow powder |
| 15 | $CH_3$ | $OCH_3$ | $CH_3$ | H | Cl | meso | yellow powder |
| 16 | $CH_3$ | OH | $CH_3$ | H | Cl | meso | pale yellow powder |
| 17 | Cl | $OCH_3$ | Cl | H | Cl | meso | pale yellow powder |
| 18 | Cl | OH | Cl | H | Cl | meso | pale yellow powder |
| 19 | Cl | $OCH_3$ | Cl | H | Cl | d,l | light yellow powder |
| 20 | Cl | OH | Cl | H | Cl | d,l | pale yellow powder |
| 21 | Cl | $OCH_3$/OH* | Cl | H | Cl | meso | yellow powder |
| 22 | Cl | $OCH_3$ | Cl | $CH_3$ | Cl | meso | pale yellow powder |
| 23 | Cl | $OCH_3$ | Cl | $CH_3$ | Cl | d,l | pale yellow powder |

TABLE 1-continued

| Ex. No. | $R_1, R_4$ | $R_2, R_5$ | $R_3, R_6$ | $R_7$ (both) | X | Configuration | Color |
|---|---|---|---|---|---|---|---|
| 24 | Cl | OH | Cl | CH$_3$ | Cl | d,l | pale yellow powder |

*One group $R_2$ is OH, the other ($R_5$) is OCH$_3$

TABLE 2

Physical properties of the compounds of Table 1

$^1$H—NMR = nuclear magnetic resonance, displacement of the protons in ppm absorption in deuterated dimethylformamide (d$_7$-DMF)/tetramethylsilane at 250 Megahertz br = broad, s = singlet, d 40 doublet, t = triplet, q = quartet, m = multiplet, J = coupling constant, J$_{1,2}$ = for example the coupling constant for C-atoms adjacent to the protons, J$_{HF}$ = for example the coupling constant which results form a HF coupling

| Compound According to Example | IR | $^1$H—NMR |
|---|---|---|
| 1 | 3280 m, 3180 m, 3120 m ($\nu$-NH); 2960 w, br (CH); 2840 w (OCH$_3$); 1615 s, 1580 s ($\delta$-NH); 340 m, 330 m (Pt—Cl) | 1.93 (s, 2 CH$_3$); 3.77 (s, 2 OCH$_3$); 4.55 (br, 2 NH); 5.34 (m, br, 2 NH); 6.06 (d, br, 2 CH); 6.64–6.73 (m, 4 Ar—H); 8.21 (d, br, 2 Ar—H) |
| 2 | 3420 s,br ($\nu$-OH); 3280 s, 3240 m, 3210 m, 3180 m, 3110 m ($\nu$-NH); 2980 w (CH); 1620 s, 1590 s ($\delta$-NH); 340 m, 330 m (Pt—Cl) | 1.87 (s, 2 Ch$_3$); 4.47 (br, 2 NH); 5.17 (m, br, 2 NH); 6.01 (d, br, 2 CH): 6.53–6.62 (m, 4 Ar—H); 8.05 (br, 2 Ar—H; 9.51 s, 2 OH) |
| 3 | 3240 s, 3210 m, 3130 m ($\nu$-NH), 2960 w, 2930 w (CH); 2830 w (OCH$_3$); 1610 s, 1580 s ($\delta$-NH); 335 m, 330 m (Pt—Cl) | 2.27 (s, 2 Ch$_3$); 370 (s, 2 OCH$_3$); 4.60 (m, br, 2 NH); 5.15 (m, br, 2 NH); 6.30 (d, br, 2 CH); 6.56 (d, J$_{1,3}$=2 Hz, 2 Ar,H); 6.78 (q, J$_{1,2}$=8 Hz, J$_{1,3}$=2 Hz, 2 Ar—H); 7.91 (d, J$_{1,2}$=8 Hz, 2 Ar—H) |
| 4 | 3350 sh, 3240 s, br, 3130 m ($\nu$-OH, $\nu$-NH); 2970 w (CH), 1630 s, 1580 s ($\delta$-NH); 340 m, br (Pt—Cl) | 2.20 (s, 2 Ch$_3$); 4.62 (m, br 2 NH); 5.12 (m, br, 2 NH); 6.21 (d, br, 2 CH); 6.43 (d, J$_{1,3}$=2 HZ, 2 Ar—H); 6.66 (q, J$_{1,2}$=8 Hz, 2 Ar—H); 7.82 (d, J$_{1,2}$=8 Hz, 2 Ar—H); 9.44 (s, br, 2 OH) |
| 5 | 3250 m, 3180 m, 3090 m ($\nu$-NH); 2960 w, 2940 w, (CH); 2830 w (OCH$_3$); 1600 s, 1580 s ($\delta$-NH); 350 m, br (Pt—Cl) | 3.81 (s, 2 OCH$_3$); 4.54 (br, 2 NH); 5.58 (m, br, 2 NH); 6.50 (d, br, 2 CH); 6.96 (q, J$_{1,2}$=9 Hz, J$_{1,3}$=3 Hz, 2 Ar—H); 7.33 (d, J$_{1,3}$=3 Hz, 2 Ar—H); 8.25 (d, br, 2 Ar—H) |
| 6 | 3380 s, br ($\nu$-OH); 3270 m, 3220 m, 3180 w, 3110 m ($\nu$-NH); 1595 s, 1525 s; ($\delta$-NH); 330 m, 320 m (Pt—Cl) | 4.48 (br, 2 NH); 5.46 (m, br, 2 NH); 6.45 (d, br, 2 CH); 6.82 (q, J$_{1,2}$=9 Hz J$_{1-3}$=3 Hz, 2 Ar—H); 7.25 (d, J$_{1,3}$=3 Hz, 2 Ar—H); 8.14 (br, 2 Ar—H); 10.05 (br, 2 OH) |
| 7 | 3250 m, 3180 m, 3090 m ($\nu$-NH); 2960 w, 2940 w (CH); 2830 w (OCH$_3$); 1605 s, 1565 s ($\delta$-NH); 330 m, br (Pt—Cl) | 3.82 (s, 2 OCH$_3$); 4.72 (br, 2 NH); 5.61 (m, br 2 NH); 6.44 (d, br, 2 CH); 6.95 (q, J$_{1,2}$=9 Hz, J$_{1,3}$=3 Hz, 2 Ar—H); 7.08 (d, J$_{1,3}$=3 Hz, 2 Ar—H); 8.38 (d, br, J$_{1,2}$=7 Hz, 2 Ar—H) |
| 8 | 3450–3390 br ($\nu$-OH); 3260 w, 3200 s, 3100 m ($\nu$-NH) 1605 s, 1580 m ($\delta$-NH); 325 w (Pt—Cl) | 4.67 (br, 2 NH); 5.52 (m, br, 2 NH); 6.38 (d, br, 2 CH); 6.80 (q, J$_{1,2}$=8 Hz, J$_{1,3}$=2 Hz, 2 Ar—H); 6.96 (d, J$_{1,3}$=2 Hz, 2 Ar—H); 8.26 (d, br, J$_{1,2}$=7 Hz, 2 Ar—H); 10.17 (br, 2 OH) |
| 9 | 3200 m, 3180 m, 3100 m ($\nu$-NH); 2960 w (CH); 2830 w (OCH$_3$); 1605 m, 1570 s ($\delta$-NH); 335 m, 325 m (Pt—Cl) | 3.82 (s, 2 OCH$_3$); 4.77 (br, 2 NH); 5.64 (m, br, 2 NH); 6.40 (d, br, 2 CH); 6.90–6.92 (m, 4 Ar—H); 8.41 (d, br, 2 Ar—H) |
| 10 | 3560 m; 3385 m ($\nu$-OH); 3265 m, 3230 m, 3200 m, 3095 m ($\delta$-NH); 1605 s, 1575 s ($\delta$-NH); 320 w (Pt—Cl) | 4.71 (br, 2 NH); 5.54 (m, br, 2 NH); 6.34 (d, br, 2 CH); 6.74–6.78 (m, 4 Ar—H); 8.32 (d, br, 2 Ar—H); 10.20 (br, 2 OH) |
| 11 | 3250 m, 3170 m, 3100 m ($\nu$-NH); 2960 w, 2940 w (CH); 2835 w (OCH$_3$); 1625 s, 1580 s ($\delta$-NH); 330 m (Pt—Cl) | 3.80 (s, 2 OCH$_3$); 4.60 (br, 2 NH); 5.61 (m, br, 2 NH); 6.30 (d, br, 2 CH); 6.67 (q, J$_{1,3}$=3 Hz, J$_{HF1,2}$=12 Hz, 2 Ar—H); 6.77 (q, J$_{1,2}$=9 Hz, J$_{1,3}$=Hz, 2 Ar—H); 8.36 (t, J$_{1,2}$=9 Hz, J$_{HF1,3}$=9 Hz, 2 Ar—H) |
| 12 | 3400 s, br ($\nu$-OH); 3260 s, 3210 s, 3105 m ($\nu$-NH); 1625 s, 1595 s ($\delta$-NH); 325 w (Pt—Cl) | 4.54 (br, 2 NH); 5.50 (m, br, 2 NH); 6.23 (d, br, 2 CH); 6.44 (q, J$_{1,3}$=2 Hz, J$_{HF1,2}$=12 Hz, 2 Ar—H); 6.63 (q, J$_{1,2}$=9 Hz, J$_{1,3}$=2 Hz, 2 Ar—H); 8.23 (t, J$_{1,2}$=9 Hz, J$_{HF1,3}$=9 Hz, 2 Ar—H); 10.17 (br, 2 OH) |
| 13 | 3200 m, br, 3100 m ($\nu$-NH); 3010 w, 2950 w (CH); 2840 w (OCH$_3$); 1620 s, 1585 s ($\delta$-NH); 330 m, br (Pt—Cl) | 3.88 (s, 2 OCH$_3$); 4.59 (br, 2 NH); 5.88 (m, br, 2 NH); 6.73 (d, br, 2 CH); 7.14 (d, J$_{1,3}$=3 Hz, 2 Ar—H); 7.20 (d, br, J$_{1,2}$=9 Hz, 2 Ar—H); 8.64 (br, 2 Ar—H) |
| 14 | 3340 br, sh ($\nu$-OH); 3140 s ($\nu$-NH); 3010 w, 2890 w (CH); 1620 m, 1580 w ($\delta$-NH); 323 w (Pt—Cl) | 4.54 (br, 2 NH); 5.77 (m, br, 2 NH); 6.67 (d, br, 2 CH); 7.02–7.06 (m, 4 Ar—H); 8.46 (br, 2 Ar—H); 10.45 (s, br, 2 OH) |
| 15 | 3540 w, br ($\nu$-OH); 3150 w, br ($\nu$-NH); 2960 w (CH); 2840 w (OCH$_3$); 1605 s, 1580 m ($\delta$-NH); 325 w (Pt—Cl) | 2.03 (s, 2 CH$_3$); 2.74 (s, 2 Ch$_3$); 3.74 (s, 2 OCH$_3$); 4.90 (m, 2 NH$_2$); 6.41 (d, br, 2 CH); 6.53 (s, 4 Ar—H) |
| 16 | 3430 s, br ($\nu$-OH); 3330 w, 3160 w ($\nu$-NH); 2960 w (CH); 1610 s, 1590 s, ($\delta$-NH); 330 m (Pt—Cl) | 1.97 (s, br, 2 CH$_3$); 2.67 (s, br, 2 CH$_3$); 4.75–4.9 (m, br, 2 NH$_2$); 6.35 (d, br, 2 CH); 6.41 (s, 4 Ar—H); 9.43 (s, 2 OH) |
| 17 | 3310 m, 3270 w, 3250 w, 3180 w, br, 3105 m ($\nu$-NH); | 3.86 (s, 2 OCH$_3$); 5.35 (m, 2 NH$_2$); 6.75 |

TABLE 2-continued

Physical properties of the compounds of Table 1
$^1$H—NMR = nuclear magnetic resonance, displacement of the protons in ppm absorption in deuterated dimethylformamide
(d$_7$-DMF)/tetramethylsilane at 250 Megahertz br = broad, s = singlet, d 40 doublet, t = triplet, q = quartet, m = multiplet,
J = coupling constant, J$_{1,2}$ = for example the coupling constant for C-atoms adjacent to the protons, J$_{HF}$ = for example the coupling
constant which results form a HF coupling

| Compound According to Example | IR | $^1$H—NMR |
|---|---|---|
|  | 3008 w, 2975 w, 2940 w (CH); 2835 w (OCH$_3$); 1602 s, 1555 s (δ-NH), 317 w (Pt—Cl) | (d, br, 2 CH); 7.01 (s, 2 Ar—H); 7.04 (s, 2 Ar—H) |
| 18 | 3370 s, br (ν-OH); 3295 m, 3245 m, 3160 m, br, 3085 w, 3060 w (ν-NH); 1607 s, 1560 s (δ-NH); 327 sh, 317 w (Pt—Cl) | 5.30 (m, 2 NH$_2$); 6.73 (d, br, 2 CH); 6.82 (s, 2 Ar—H); 6.85 (s, 2 Ar—H); 10.86 (s, 2 OH) |
| 19 | 3290 s, 3190 s, 3100 w, br (ν-NH); 2955 w, 2930 w (CH); 2830 (OCH$_3$); 1600 s, 1552 s (δ-NH); 335 m, 322 m (Pt—Cl) | 3.86 (s, 2 OCH$_3$); 4.99 (m, 2 NH); 5.58 (m, 2 NH); 6.90 (d, br, 2 CH); 6.96 (d, J=2 Hz, 2 Ar—H); 7.19 (d, J=2 Hz, 2 Ar—H) |
| 20 | 3240 s, br (ν-OH); 3300 s (ν-NH); 2880 w (CH); 1610 s, 1572 s (δ-NH); 335 sh, 328 w (Pt—Cl) | 4.92 (m, 2 NH); 5.50 (m, 2 NH); 6.88 (d, br, 2 CH); 6.78 (d, J=2 Hz, 2 Ar—H); 6.98 (d, J=2 Hz, 2 Ar—H); 10.57 (s, 2 OH) |
| 21 | 3270 s, 3230 w, 3190 w (ν-NH); 2960 w, 2940 w (CH); 2840 w (OCH$_3$); 1615 s, 1585 m, (δ-NH); 325 w (Pt—Cl) | 3.86 (s, 1 OCH$_3$); 5.25–5.45 (m, br, 2 NH$_2$); 6.75 (br, 2 CH); 6.82 (s, 1 Ar—H); 6.85 (s, 1 Ar—H); 7.01 (s, 1 Ar—H); 7.04 (s, 1 Ar—H); 10.89 (s, 1 OH) |
| 22 | 3290 m, 3160 m, 3090 w (ν-NH); 2960 w (CH); 1600 s, 1555 s (δ-NH); 345 m, br (Pt—Cl) | 2.92 (s, 2 CH$_3$); 3.88 (s, 2 OCH$_3$); 5.04 (t, J=2 Hz, 1 NH); 5.06 (t, J=2 Hz, 1 NH); 6.05 (m, br, 2 CH); 7.06 (d, J$_{1,3}$=3 Hz, 2 Ar—H); 7.13 (d, J$_{1,3}$=3 Hz, 2 Ar—H) |
| 23 | 3280 m, 3200 m, 3080 w (ν-NH); 2990 w, 2940 m (CH); 1600 s, 1560 s, (δ-NH); 340 m, 335 sh (Pt—Cl) | 2.74 (s, 2 CH$_3$); 5.43 (t, J=3 Hz, 1 NH); 5.45 (t, J=3 Hz, 1 NH); 5.94 (m, br 2 CH); 7.04 (d, J$_{1,3}$=3 Hz, 2 Ar—H); 7.23 (d, J$_{1,3}$=3 Hz, 2 Ar—H) |
| 24 | 3330 s, br (ν-OH); 3230 m, 3190 m (ν-NH); 2940 w (CH); 1610 s, 1570 s (δ-NH); 340 m, 330 m (Pt—Cl) | 2.75 (s, 2 CH$_3$); 5.36 (t, J=3 Hz, 1 NH); 5.39 (t, J=3 Hz, 1 NH); 5.87 (d, br, 2 CH); 6.82 (d, J$_{1,3}$=3 Hz, 2 Ar—H); 7.00 (d, J$_{1,3}$=3 Hz, 2 Ar—H); 10.85 (br, 2 OH) |

EXAMPLE 25 meso-Dichloro-[1,2-bis-(2,6-dichloro-phenyl) ethylendiamine]-platinum-(II)

Production was carried out according to the stated general directions in aqueous medium. The material is a light yellow powder.

IR-Spectrum in KBr: 3375 w, 3315 m, 3280 w, 3225 m, 3200 w, 3060 w (νNH); 2960 w (CH); 1580 m, 1562 m (δNH); 325 sh, 317 w ( Pt-Cl).

$^1$H-NMR: δ=5.50 (m, 2 NH$_2$); 6.86 (d, br, 2 CH); 7.30–7.52 (m, 6 Ar—H).

EXAMPLE 26 d,l-Dichloro-[1,2-bis[2-6-dichloro-phenyl)-ethylenediamine]-platinum-(II)

Production was carried out according to the stated general directions in aqueous medium. the material is a yellow powder.

IR-specturm in KBr: 3300 s, 3195 m, br, 3100 w, 3060 w (νNH); 3000 w (CH); 1580 s, 1562 s (δNH); 330 sh, 322 m (Pt-Cl).

$^1$H-NMR: δ=5.15 (m, 2NH); 5.72 (m, br, 2 NH); 7.00 (d, br, 2 CH); 7,31–7.60 (m, 6 Av—H).

Synthesis of Pt Complexes According to Examples 27–32

830 mg (2 mmoles) of K$_2$PtCl$_4$ dissolved in 8 ml of water were dropped into a solution of 2 mmoles of the corresponding 1,2-diphenyl-ethylenediamine dihydrochloride in about 10 ml of water. The solution was brought to pH 5.5–6.5 with NaOH. Stirring was carried out at room temperature with the exclusion of light and the solution was neutralized at 1–2 hour intervals. The end of the reaction was shown by a constant pH. The product was filtered off with suction, washed free of chloride water and dried.

EXAMPLE 27

(±)-Dichloro-[1,2-bis(4-fluoro-phenyl)ethylendiamine]-platinum-(II) ((±) 4-F)

Yellow powder M.P. about 380° C. (Decomposition) IR-Spectrum in KBr: 3270 s, 3190 s (NH$_2$), 1610 s, 1515 s, 1240 s, 1170 m, 840 m, 320 w. $^1$H-NMR: δ=5.05 (broad, 2H, NH); 5.90 (br, 2H, NH); 6.50 (d, 2H, CH); 7.06 (t, J$_{HH}$=8.8 Hz, J$_{HF}$=8.9 Hz 4H, meta H); 7.74 (q, J$_{HH}$=8.8 Hz, J$_{HF}$=5.4 Hz, 4 H, ortho H).

The starting material is produced for example as follows:

19.9 mmoles of 1-azido-2-amino-1,2-bis-(4-fluorophenyl)-ethane were dissolved in about 60 ml of absolute ether and under ice cooling dropped into 1.52 grams (40 mmoles of LiAlH$_4$ in 60 ml of absolute ether. After heating at reflux for 4.5 hours the product was cooled and hydrolyzed at 0°–5° C. with wet ether and a little water. It was filtered with suction from aluminum hydroxide and this was extracted several times with methylene chloride. After removal of the solvent their remained bis(4-fluorophenyl)ethylenediamine as an oil. IR (Film/Base): 3380 m, 3300 m (NH), 1600 s, 1510 s, 1220 s, 830 s.

The 1-azida-2-amino-1,2,-bis-4-fluorophenyl) ethane was obtained from 4,4-difluorostilbene via the aziridine analogous to the directions stated in German OS No. 3405611 (pages 17–19). The carbonate obtained as an intermediate product thereby was further processed without additional purification. The 2,3-bis(4-fluorophenyl)-aziridine was purified by chromatography on silica gel 60 with benzene/methylene chloride as eluation agent. Besides the cis-aziridine there was obtained a little trans-aziridine.

IR (Film): 3300 m (NH), 1610 s, 1510 s, 1220 s.

EXAMPLE 28

(±)-dichloro-[1,2-bis(4-chloro-phenyl)-ethylene diamine]-platinum (II) ((±) 4-CL)

Yellow powder, MP.P about 370° C. (Decomposition) IR-Spectrum in KBr: 3210 s, 3190 s, 3100 m ($NH_2$), 1600 m, 1560 m, 1495 s, 1415 m, 1090 s, 1015 s, 825 s, 600 s, 520 m, 320 m (Pt-Cl).

$^1$H-NMR: $\delta$=5.55 (br, 2H, NH); (br, 2H, NH); 6.72 (d, 2H, CH); 7.34 (d, J=8.5 Hz, 4H meta H); 7.86 (d, J=8.5 Hz, 4H; ortho H).

The starting amine was obtained according to Method C.

EXAMPLE 29 meso-Dichloro-[1,2-bis(4-chlorophenyl)ethylenediamine]-platinum (II) (meso 4-Cl)

Yellow powder, M.P. about 315° C. (Decomposition) IR-spectrum in KBr: 3240 s, 3180 s, 3100 m, 3020 m ($NH_2$); 1550 s, 1170 s, 1040 s, 812 s, 770, 315 m (Pt-Cl).

$^1$H-NMR: $\delta$=4.65 (br, 2H, NH); 5.79 (br, 2H, NH); 6.25 (d, 2H, CH); 7.34 (d, J=8 Hz, 4H, meta H); 7.64, 7.68 (d, J=8 Hz, 4H, ortho H).

The starting amine was obtained according to Method B.

EXAMPLE 30

(±)-Dichloro-[1,2-bis(3-chloro-phenyl)-ethylenediamine]-platinum (II) ((±) 3-Cl)

Yellow powder IR-Spectrum in KRr: 3260 s, 3200 s, ($NH_2$), 1600 m, 1575 s, 1480 m, 1440 m, 790 s, 720 m, 690 s, 440 w, 310 m (Pt-Cl).

$^1$H-NMR: $\delta$- 5.39 (broad, 2H NH); 6.14 (broad, 2H, NH); 6.62 (d, 2H, CH); 7.29–7.88 (m, 8H, aromatic H).

The starting material can be obtained from 3,3'-dichlorostilbene via the corresponding cis-1,2-bis-(3-chloro-phenyl)-aziridine and the threo-1-azido-2-animo-1,2-bis-(3-chloro-phenyl)ethane analogous to the directions given in German OS No. 3405611, pages 17–19.

EXAMPLE 31 meso-Dichloro-[1,2-bis(3-chloro-phenyl)-ethylenediamine]-platinum(II) (meso 3-Cl)

Reaction time: 3 days

Yellow Powder IR-Spectrum in KBr.: 3240 s, 3180 s, 3100 m, 3020 m ($NH_2$), 1550 m, 1170 s, 1040 s, 812 s, 770 s, 315 m (Pt-Cl).

$^1$H-NMR: $\delta$=4.64 (broad 2H, NH); 5.91 (broad, 2H, NH); 6.26 (d, 2H, CH); 7.27–7.78 (m, 8H aromatic H).

The starting amine is not known.

EXAMPLE 32 meso-Dichloro-[1,2-bis(3-fluoro-phenyl)-ethylenediamine]-platinum(II) (meso 3-F)

Synthesis with addition of tertiary butanol.

Yellow powder IR-Spectrum in KBr.: 3200 s, 3120 s, ($NH_2$), 1630 m, 1600 s, 1500 m, 1460 m, 780 s, 700 s, 520 w, 320 m (Pt-Cl).

$^1$H-NMR: $\delta$- 4.73 (broad, 2H, NH); 5.87 (broad, 2H, NH); 6.30 (d, 2H, CH); 7.08–7.16 (m, 2H, aromatic H); 7.28–7.39 (m, 4H, aromatic H); 7.58–7.62 (d, 2H, aromatic H).

The starting material is obtained according to Method B.

EXAMPLE 33 meso-Dichloro-[1,2-bis(4-fluoro-phenyl)-ethylendiamine]-platinum (II) (meso 4F)

248 mg (1 mmole) of meso-1,2-bis(4-fluorophenyl)-ethylenediamine were dissolved in 40 ml of 50% tertiary butanol with heating. There was dropped into the solution 415 mg of $K_2PtCl_4$ dissolved in 10 ml of water. Stirring was carried out for 5 hours at 50°–60° C. with the exclusion of light, subsequently the product was filtered off with suction, washed with tertiary butanol and water and dried. Yellow powder, M.P. about 305° C. (Decomposition).

IR-Spectrum in KBr:3250 s, 3190 s, 3120 s ($NH_2$), 1610 s, 1560 s, 1515 s. 1230 s. 805 s. 325 m.

$^1$H-NMR: $\delta$=4.53 (br, 2H, NH); 5.69 (br, 2H, NH); 6.20 (d, 2H, CH); 7.10 (t, $J_{HH}$=8.8 Hz, $J_{HF}$=8.9, 4H, meta H); 7.64 (q, $J_{HH}$=8.8 Hz, $J_{HF}$=5.4 Hz, 4H, ortho H).

The starting amine is known.

EXAMPLES 34–40

Examples of the Anion X by Another Anion

Diaquo-meso-1,2-bis(2,6-dichloro-4-hydroxyphenyl)-ethylene-diamine-platinum(II)-sulfate 194 mg (0.3 mmole of meso-1,2-bis)2,6-dichloro-4-hydroxy-phenyl)-ethylenediamine-dichloroplatinum-(II)-complex were suspended with 93 mg (0.3 mmoles) of silver sulfate in 60 ml of water in an ultrasonic bath and stired for 3 days at 50° C. with exclusion of light. The AgCl which formed and the unreacted meso-1,2-bis(2,6-dichloro-4-hydroxyphenyl)-ethylenediamine-dichloro-platinum(II) complex were filtered off with suction over a membrane filter. After the suction filtering there remained an aqueous solution which was concentrated on the oil pump to dryness. The residue was digested with absolute methanol, whereby the complex went into solution and thus can be separated from unreacted $Ag_2SO_4$. The methanolic solution was concentrated as far as possible and the complex precipitated with diisopropyl ether. The precipitate was filtered off with suction, washed with a lot of diisopropyl ether and dried over $P_2O_5$ at room temperature. White powder, soluble in water; Yield: 80 mg (38% of theory)

EXAMPLE 35

Diaquo-meso-1,2-bis(4-fluorophenyl)ethylenediamine-platinum(II)-sulfate 514 mg (1 mmole of the corresponding dichloro complex were suspended with 310 mg (1 mmole) of silver sulfate in 60 ml of water in an ultrasonic bath and stirred for 3 days at 50° C. with the exclusion of light. The AgCl formed and the unreacted dichloro complex were removed with suction over a membrane filter. There remained a yellow solution which was concentrated on the oil pump to dryness. The residue was digested with absolute methanol whereby the complex went into solution and so can be filtered off from the unreated $Ag_2SO_4$. The methanolic solution was concentrated and the complex precipitated with diisopropyl ether. The precipitate was filtered with suction, washed with a lot of diisopropyl ether and dried over $P_2O_5$ at room temperature.

White powder; Yield: 307 mg (52% of theory).

The following sulfates were produced analogous to the described diaquo-meso-1,2-bis(4-fluoro-phenyl)-ethylenediamine-platinum(II)-sulfate.

EXAMPLE 36

Diaquo-d,l-1,2-bis(4-fluorophenyl)ethylenediamine-platinum-(II)-sulfate

Starting material:
514 mg (1 mmole) of the corresponding dichloro-complex,
310 mg (1 mmole) of $Ag_2SO_4$ White powder;
Yield: 160 mg (26% of theory).

EXAMPLE 37

Diaquo-meso-1,2-bis(3-hydroxyphenyl)ethylenediamine-platinum-(II)-sulfate

Starting material:
693 mg (1 mmole) of the corresponding diiodo complex
310 mg (1 mmole) $Ag_2SO_4$ White powder;
Yield: 437 mg (77% of theory).

The diiodo-starting complex meso-1,2-bis-(3-hydroxyphenyl)-ethylenediamine-diiodo-platinum-(II) was produced for example as follows:

4 grams of KI and 420 mg (1 mmole) of $K_2PtCl_6$ were dissolved in 10 ml of water and stirred for 20 minutes. This solution was dropped into a suspension of 244 mg (1 mmole) of meso-1,2-bis-(3-hydroxy-phenyl)-ethylenediamine in a 50% tert.butanol/water mixture and stirred for 18 hours at 50° C. with the exclusion of light. The complex was filtered off with suction, washed with 0.1N H and warm water and dried over $P_2O_5$, yellow powder;
Yield: 634.5 mag (92% of theory).

EXAMPLE 38

Diaquo-d,l-1,2-bis(3-hydroxyphenyl)ethylenediamine-platinum(II-sulfate

Starting material:
693 (1 mmole) of the corresponding diiodo-complex,
310 (1 mmole) $Ag_2SO_4$ Light yellow powder;
Yield: 513 mg (90% of theory).

The diiodo starting complex is obtained analogous to Example 37.

EXAMPLE 39

Diaquo-meso-1,2-bis(2-fluoro-4-hydroxyphenyl)ethylenediamine-platinum(II)-sulfate Starting material:
526 mg (1 mmole) of the corresponding dichloro-complex,
310 mg (1 mmole) $Ag_2SO_4$ White powder;
Yield: 600 mg (98% of theory).

EXAMPLE 40

Diaquo-meso-1,2-bis(2,6-dichloro-4-hydroxyphenyl)ethylenediamine-platinum(II)-sulfate Starting material:
194 mg (0.3 mmole) of the corresponding dichloro-complex,
93 mg (0.3 mmole) $Ag_2SO_4$ White powder;
Yield: 80 mg (38% of theory).

Examples of Pharmaceutical Preparations Example (Lyophilizate)

There were dissolved with stirring in 800 ml of water for injection purposes 10 grams of D-mannitol and 3 grams of diaquo-meso-[1,2-bis(2,6-dichloro-4-hydroxyphenyl)-ethylenediamine]-platinum(II)-sulfate and the volume filled up to 1 liter with water for injection purposes.

This solution was sterile filtered under aseptic conditions over a membrane filter having a pore size of 0.22 $\mu$m and filled to 10 ml in 15 ml injection flasks of hydrolytic class I. The flasks were provided with freeze dry stoppers and lyophilized in a suitable apparatus. After the dyring gassing was carried out with dried nitrogen and the flasks closed in the apparatus. The stoppers were secured by an edge cap.

For the intravenous use the lyophilizate was reconstituted in 10 ml of injection water.

1 ml of solution contains 3 mg of active material.

EXAMPLE (TABLETS)

200 g d,l-dichloro-[1,2-bis-(2,6-dichloro-4-hydroxyphenyl)-ethylenediamine]-platinum (II) (corresponding to Example 20), 500 g lactose, 360 g microcrystalline cellulose, 130 g corn starch and 10 g magnesium stearate were passed through a sieve having a mesh width of 0.8 mm and homogenized. This composition was pressed in known manner to tablets of 120 mg, 1 tablet contains 20 mg of active material.

EXAMPLE (COATED TABLETS)

For the production of film tablets, tablet according to the preceding example with the help of a spraying apparatus in known manner were provided with stomach or small intestine soluble coating which can consist of a suitable polymeric film former, such as for example, acrylate esters or methacrylate ester and suitable adjuvants such as wetting agents, plasticizers, dyestuffs, lubricants, etc. The tablets also can be processes in customary manner to dragees.

The entire disclosure of German priority application No. P 3506507.9 is hereby incorporated by reference.

What is claimed is:
1. A (1,2-diphenyl-ethylenediamine)-platinum(II) complex of the formula

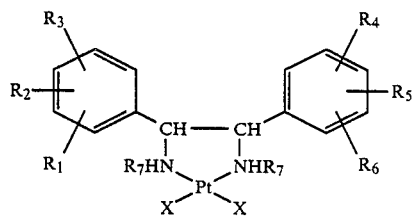

wherein $R_7$ is hydrogen or $C_1$–$C_6$-alkyl and $R_2$ is either (1) a halogen atom and the groups $R_1$, $R_3$, $R_4$, $R_5$, and $R_6$ are the same or different and are hydrogen, halogen, trihalomethyl, $C_1$–$C_6$-alkyl, hydroxy, $C_1$–$C_6$-alkoxy, a $C_2$–$C_6$-alkanoyloxy or a halo or $C_1$–$C_4$-alkanesulfonyloxy substituted $C_2$–$C_6$-alkanoyloxy group or $R_2$ is in the 4-position and is (2) a hydroxy group, a $C_1$–$C_6$-alkoxy group, a $C_2$–$C_6$-alkanoyloxy group or a halo or $C_1$–$C_4$-alkanesulfonyloxy substituted $C_2$–$C_6$-alkanoyloxy group and if $R_2$ is (2) then the groups $R_1$ and $R_3$ which are the same or different are in the 2 and 6 positions of the phenyl group and are halogen, trihalomethyl, $C_1$-$C_6$-alkyl, hydroxy, a $C_1$-$C_6$-alkoxy, $C_2$-$C_6$-alkanoyloxy group or a halo or $C_1$-$C_4$-alkanesulfonyloxy substituted $C_2$-$C_6$-alkanoyloxy group with the proviso that $R_1$ can also be hydrogen* and the groups $R_4$, $R_5$, and $R_6$ are the same or different and are hydrogen, halogen, trihalomethyl, $C_1$-$C_6$-alkyl, hydroxy, $C_1$-$C_6$-alkoxy, a $C_2$-$C_6$-alkanoyloxy group or a halo or $C_1$-$C_4$-alkanesulfonyloxy substituted $C_2$-$C_6$-alkanoyloxy group and X is the equivalent of a physiologically compatible anion.
*if $R_3$ is halogen, trihalomethyl or $C_1$-$C_6$-alkyl 2. A compound according to claim 1 wherein $R_1$ is OH, $C_1$-$C_6$-alkoxy a $C_2$-$C_6$-alkanoyloxy group, or a $C_2$-$C_6$-alkanoyloxy group substituted by halogen, or by $C_1$-$C_4$-alkanesulfonyloxy;

$R_1$ and $R_3$ are halogen, trihalomethyl, $C_1$-$C_6$-alkyl, OH, $C_1$-$C_6$-alkoxy, a $C_2$-$C_6$-alkanoyloxy group, a $C_2$-$C_6$-alkanoyloxy group substituted by halogen or by $C_1$-$C_4$-alkanesulfonyloxy, with the proviso that $R_1$ can also be hydrogen if $R_3$ is halogen, trihalomethyl or $C_1$-$C_6$-alkyl;

$R_4$, $R_5$, and $R_6$ are hydrogen, halogen, trihalomethyl, $C_1$-$C_6$-alkyl, OH, $C_1$-$C_6$-alkoxy, a $C_2$-$C_6$-alkanoyloxy group, $C_2$-$C_6$-alkanoyloxy substituted by halogen or $C_1$-$C_4$-alkanesulfonyloxy and $R_7$ is H or $C_1$-$C_6$-alkyl.

3. A compound according to claim 1 wherein at least one of the groups $R_1$, $R_2$, and $R_3$ is a halogen atom, the remaining groups $R_2$ and $R_3$ are the same or different and can be hydrogen or a halogen atom, while the groups $R_4$, $R_5$, and $R_6$ are either all hydrogen or are hydrogen and halogen.

4. A compound according to claim 1 wherein at least one of $R_1$, $R_2$ and $R_3$ is halogen or trifluoromethyl.

5. A compound according to claim 1 wherein either none of $R_1$, $R_2$ and $R_3$ is hydrogen or none of $R_4$, $R_5$ and $R_6$ is hydrogen.

6. A compound according to claim 5 wherein none of $R_1$, $R_2$ and $R_3$ is hydrogen.

7. A compound according to claim 1 wherein $R_2$ is halogen.

8. A compound according to claim 7 wherein $R_2$ is chlorine.

9. A compound according to claim 1 wherein $R_2$ is trifluoromethyl.

10. A compound according to claim 1 having the formula

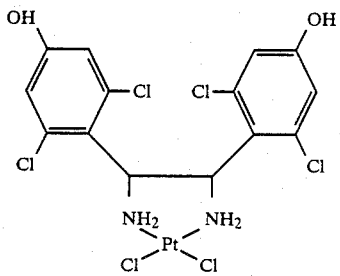

11. The meso form of the compound of claim 10.
12. The d, l form of the compound of claim 10.
13. A compound according to claim 1 having the formula

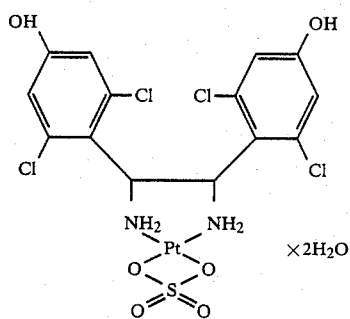

14. The meso form of the compound of claim 13.